(12) United States Patent  (10) Patent No.: US 6,219,059 B1
Argiro  (45) Date of Patent: Apr. 17, 2001

(54) INTERACTIVE CONTROL OF VOXEL ATTRIBUTES USING SELECTABLE CHARACTERISTICS

(75) Inventor: Vincent J. Argiro, Fairfield, IA (US)

(73) Assignee: Vital Images, Inc., Plymouth, MN (US)

(*) Notice: Subject to any disclaimer, the term of this patent is extended or adjusted under 35 U.S.C. 154(b) by 0 days.

(21) Appl. No.: 08/950,729

(22) Filed: Oct. 15, 1997

Related U.S. Application Data

(63) Continuation-in-part of application No. 08/731,535, filed on Oct. 16, 1996.

(51) Int. Cl.$^7$ .................................................. G06T 15/00
(52) U.S. Cl. ............................................. 345/424; 345/426
(58) Field of Search .................................. 345/424, 425, 345/422, 426; 382/131

(56) References Cited

U.S. PATENT DOCUMENTS

| Re. 35,798 | 5/1998 | Kimura ................................. 345/424 |
| 5,293,313 | 3/1994 | Cecil et al. ....................... 364/413.22 |
| 5,297,215 | 3/1994 | Yamagishi ................................ 382/6 |
| 5,305,204 | * 4/1994 | Ohhashi ............................... 382/131 |
| 5,319,551 | * 6/1994 | Sekiguchi et al. ................... 382/131 |
| 5,381,518 | 1/1995 | Drebin et al. ........................ 395/124 |
| 5,452,416 | 9/1995 | Hilton et al. ......................... 395/161 |
| 5,488,952 | 2/1996 | Schoolman ...................... 178/660.07 |
| 5,493,595 | 2/1996 | Schoolman ............................ 378/41 |
| 5,515,484 | * 5/1996 | Sfarti et al. .......................... 345/424 |
| 5,542,003 | 7/1996 | Wofford .............................. 382/132 |
| 5,544,283 | 8/1996 | Kaufman et al. .................... 395/124 |
| 5,557,711 | 9/1996 | Malzbender ........................ 395/122 |
| 5,566,279 | 10/1996 | Katayama ............................ 395/119 |
| 5,590,214 | 12/1996 | Allen ................................... 382/128 |
| 5,602,891 | 2/1997 | Pearlman .............................. 378/62 |
| 5,605,153 | 2/1997 | Fujioka et al. .................... 128/653.1 |
| 5,630,034 | 5/1997 | Oikawa et al. ...................... 395/124 |
| 5,647,360 | 7/1997 | Bani-Hashemi et al. ......... 128/653.1 |

(List continued on next page.)

FOREIGN PATENT DOCUMENTS

| 0368425 | 5/1990 | (EP) . |
| 0635797 | 1/1995 | (EP) . |
| 94/23375 | 10/1994 | (WO) . |

OTHER PUBLICATIONS

"Picker International Homepage, epi–Volume Product Data", ,http://www.picker.com>., 1–4, (1996).

"Voxel View: Vital Images, Optimizing the Value of Medical Imaging", *Brochure: Vital Images Inc.,* Fairfield, Iowa, (1995).

Argiro, V., "Seeing in VOlume", *PIXEL*, 35, 38–39, (Jul./Aug. 1990).

(List continued on next page.)

*Primary Examiner*—Mark K. Zimmerman
*Assistant Examiner*—Albert K. Lee
(74) *Attorney, Agent, or Firm*—Schwegman, Lundberg, Woessner & Kluth, P.A.

(57) ABSTRACT

Controlling the attributes (such as transparency) of volume-rendered images via a window/level mechanism when the images are displayed is disclosed. A volume-rendered image includes a set of voxel data representing an object. The set of voxel data has a range of voxel values, and each voxel datum (or voxel) has at least a voxel value and an attribute value (such as a transparency value). In one embodiment, a computerized system includes a characteristic selector, a level point and window set, and a viewer. The characteristic selector permits a user to select a characteristic to control an attribute of the set of voxel data, such as transparency. The level point and window set permits the user to set the level point and the window within the range of voxel values, where the window is centered at the level point and the characteristic is at least applicable within the window. The viewer displays the set of voxel data, such that the attribute values of voxel data having voxel values within the window are changed as governed by the characteristic selected. Desirably, the characteristics are predetermined in a clinical manner to promote optimal viewing.

20 Claims, 4 Drawing Sheets

U.S. PATENT DOCUMENTS

| | | | |
|---|---|---|---|
| 5,734,384 | * 3/1998 | Yanof et al. | 345/424 |
| 5,737,506 | 4/1998 | McKenna et al. | 395/125 |
| 5,782,762 | * 7/1998 | Vining | 600/407 |
| 5,807,448 | * 9/1998 | Nakazawa | 156/58 |
| 5,825,908 | * 10/1998 | Pieper et al. | 382/131 |
| 5,986,662 | * 11/1999 | Argiro et al. | 345/424 |
| 5,995,108 | * 11/1999 | Isobe et al. | 345/421 |

OTHER PUBLICATIONS

Argiro, V., et al., "VOXELS: Data in 3–D", *BYTE*, 177–180, 182, (May 1992).

Cutner, N., "The Breakthrough", 71–72, 74.

Drebin, R.A., et al., "Volume Rendering", *Computer Graphics*, vol. 22, No. 4, 65–74, (Aug. 1988).

Frenkel, K.A., "Volume Rendering", *Communications of the ACM*, vol. 32, No. 4, 426–435, (Apr. 1989).

Gher, M.E., et al., "The Accuracy of Dental Radiographic Techniques Used for Evaluation of Implant Fixture Placement", *The International Journal of Periodontics & Restorative Dentistry*, vol. 15, No. 3, 269–283, (1995).

Kaufman, A., "Chapter 1: Introduction to Volume Visualization", *IEEE*, 1–18, (1991).

Kiely, T., "Beholding the Brain", *Computer Graphics World*, 26–32, (Dec. 1991).

Kupfer, A., "New Images of Babies Before Birth", *Fortune*, 87, (Aug. 9, 1993).

Laur, D., et al., "Hierarchical Splatting: A Progressive Refinement Algorithm for Volume Rendering", *Computer Graphics*, vol. 25, No. 4, 285–288, (Jul. 1991).

Levoy, M., "Volume Rendering: Display of Surfaces from Volume Data", *IEEE Computer Graphics & Applications*, 148–156, (May 1988).

LoPiccolo, P., "The Visible Volume", *Computer Graphics World*, 47, unnumbered, 51, (Apr. 1991).

Mahoney, D.P., "Internal Medicine", *Computer Graphics World*, 47–54, (Apr. 1991).

Mahoney, D.P., "Small Worlds", *Computer Graphics World*, 57–58, (Apr. 1991).

Rubin, G.D., et al., "Perspective Volume Rendering of CT and MR Images: Applications for Endoscopic Imaging", Reprinted from *Radiology*, vol. 199, No. 2, 321–330, (May 1996).

Snider, M., "Computer modeling lets physician 'inside' patient", *USA Today*.

Stapleton, L., "From the Inside Out", *Computer Graphics World*, 89–92, (Apr. 1992).

Van Zandt, W., et al., "A New 'Inlook' on Life", *UNIX Review*, vol. 7, No. 3, 52, 54–57, (Mar. 1989).

VanZandt, W., "Scientific Visualization: One Step in Lab Analysis Workflow", *Advanced Imaging*, 21–22, 73, (Feb. 1992).

Westover, L., "Footprint Evaluation for Volume Rendering", *Computer Graphics*, vol. 24, No. 4, 267–376, (Aug. 1990).

Wilhelms, J., et al., "A Coherent Projection Approach for Direct Volume Rendering", *Computer Graphics*, vol. 25, No. 4, 275–283.

* cited by examiner

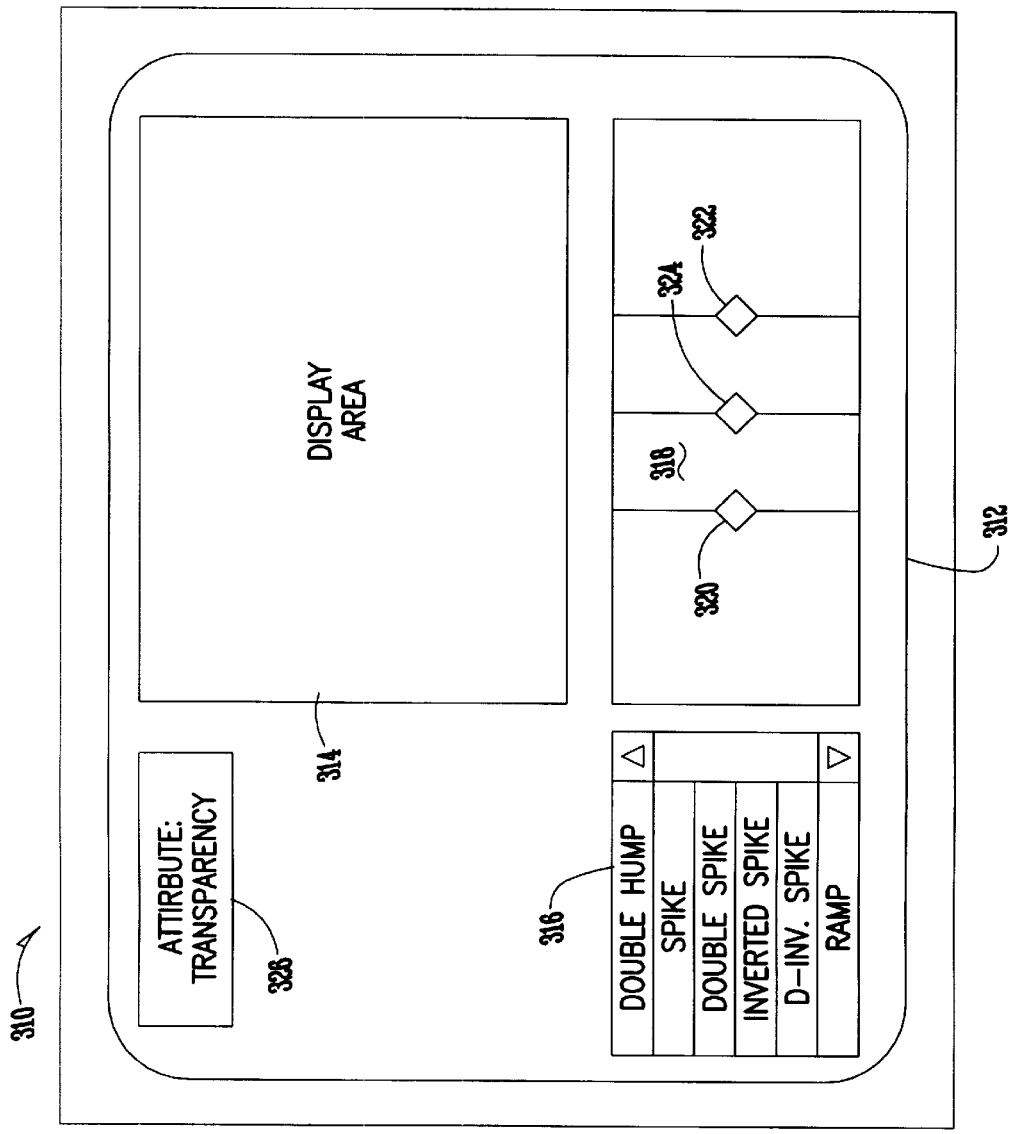

INTERACTIVE CONTROL OF VOXEL ATTRIBUTES USING SELECTABLE CHARACTERISTICS

RELATED APPLICATIONS

This application is a continuation-in-part of U.S. application Ser. No. 08/731,535, filed on Oct. 16, 1996, and entitled "Advanced Diagnostic Viewer," which is hereby incorporated by reference.

FIELD OF THE INVENTION

The present invention relates generally to the display of images that are three-dimensional volume renderings, and more particularly to controlling the attributes of such images via a window/level mechanism when the images are displayed.

BACKGROUND OF THE INVENTION

Because of the increasingly fast processing power of modern-day computers, users have turned to computers to assist them in the examination and analysis of images of real-world data. For example, within the medical community, radiologists and other professionals who once examined x-rays hung on a light screen now use computers to examine images obtained via ultrasound, computed tomography (CT), magnetic resonance (MR), ultrasonography, positron emission tomography (PET), single photon emission computed tomography (SPECT), magnetic source imaging, and other imaging techniques. Countless other imaging techniques will no doubt arise as medical imaging technology evolves.

Each of the above-identified imaging procedures generates volume images, although each relies on a different technology to do so. Thus, CT requires an x-ray source to rapidly rotate around a patient to obtain up to hundreds of electronically stored pictures of the patient. Conversely, for example, MR requires that radio-frequency waves be emitted to cause hydrogen atoms in the body's water to move and release energy, which is then detected and translated into an image. Because each of these techniques penetrates the body of a patient to obtain data, and because the body is three-dimensional, this data represents a three-dimensional image, or volume. In particular, CT and MR both provide three-dimensional "slices" of the body, which can later be electronically reassembled.

Computer graphics images, such as medical images, have typically been modeled through the use of techniques such as surface rendering and other geometric-based techniques. Because of known deficiencies of such techniques, researchers have turned to volume-rendering techniques as a more accurate way to render images based on real-world data. Volume-rendering takes a conceptually intuitive approach to rendering, by assuming that three-dimensional objects are composed of basic volumetric building blocks.

These volumetric building blocks are commonly referred to as voxels. Whereas, by contrast, the well known pixel is a picture element—i.e., a tiny two-dimensional sample of a digital image have a particular location in the plane of a picture defined by two coordinates—a voxel is a sample that exists within a three-dimensional grid, positioned at coordinates x, y, and z. The voxel has a "voxel value," as that value is obtained from real-world scientific or medical instruments. The voxel value may be measured in any of a number of different units, such as hounsefield units, which are well known to those of ordinary skill within the art.

Furthermore, for a given voxel value, a transparency value, to indicate its opacity, as well as a color value, to indicate its color, may also be assigned (for example, in a particular tabling including such mappings). Such transparency and color values may be considered attribute values, in that they control various attributes (transparency, color, etc.) of the set of voxel data that makes up an image.

Using volume-rendering, any three-dimensional volume can be simply divided into a set of three-dimensional samples, or voxels. Thus, a volume containing an object of interest is dividable into small cubes, each of which contain some piece of the original object. This continuous volume representation is transformable into discrete elements by assigning to each cube a voxel value that characterizes some quality of the object as contained in that cube.

The object is thus summarized by a set of point samples, such that each voxel is associated with a single digitized point in the data set. As compared to mapping boundaries in the case of geometric-based surface-rendering, reconstructing a volume using volume-rendering requires much less effort and is more intuitively and conceptually clear. The original object is reconstructed by the stacking of voxels together in order, so that they accurately represent the original volume.

Although more simple on a conceptual level, and more accurate in providing an image of the data, volume-rendering is nevertheless still complex. A key requisite of volume rendering is the use of the entire voxel data set to create an image. In one method of voxel rendering, called image ordering or ray casting, the volume is positioned behind the picture plane, and a ray is projected perpendicularly from each pixel in the picture plane through the volume behind the pixel. As each ray penetrates the volume, it accumulates the properties of the voxels it passes through and adds them to the corresponding pixel. The properties accumulate more quickly or more slowly depending on the transparency of the voxels.

In another method, called object-order (or compositing or splatting), the voxel values are also combined to produce image pixels for display on a computer screen. The image plane is positioned behind the volume, and each pixel is assigned an initial background value. A ray is projected perpendicularly from the image plane through the volume to the viewer. As the ray encounters each successive layer of voxels, the voxel values are blended into the background, forming the image according to each voxel's interpreted opacity. The image rendered in this method as well depends on the transparency of the voxels.

Due to such variables present in the volume-rendering process, such as attributes like transparency as has been described, volume-rendering does not by itself ensure that the resulting image of data is visually realistic or is the image desired by the end user. The volume-rendering must be conducted correctly to ensure that the image is generated accurately. Moreover, different uses of the resulting image are such that the volume-rendering be performed differently from one use to another. For example, the volume-rendering of cardiac tissue requires different opacity presets than does the volume-rendering of bone mass.

Furthermore, even within respect to the same use, volume-rendering may be required to be performed differently depending on the application of that use. For example, one physician may be interested in the most dense cardiac tissue of a data set, while another physician may be interested in the least dense cardia tissue of the data set. In either case, the volume-rendering is conducted differently to accentuate the desired features of the data. Color is also often added to emphasize the desired features.

Unfortunately, however, the end users who can most benefit from the advantages of volume-rendering are not typically volume-rendering computer graphics experts. With respect to images rendered from sets of medical data (such as patient studies), the end user who can most benefit from volume-rendering techniques are physicians, such as radiologists, and technicians. Volume-rendering enables such users to have access to medical images that may display indicia of disease and medical problems otherwise unavailable to these doctors and technicians.

A physician, however, cannot be expected to master the subtleties of volume-rendering as a computer graphics expert may be expected to. Providing physicians with a volume-rendering tool is ineffective if that tool is not easy to use, and does not permit the physician to quickly conduct a volume-rendering of an image of medical data with the correct presets and in the correct manner. Thus, any manner by which the viewing of volume-rendering is made easier or more intuitive for such users is desirable.

SUMMARY OF THE INVENTION

The above-identified shortcomings, problems, and disadvantages found in the prior art, as well as other shortcomings, problems, and disadvantages, are addressed by the present invention. The invention relates to controlling the attributes of volume-rendered images (such as transparency)via a window/level mechanism when the images are displayed. A volume-rendered image includes a set of voxel data that represents an object. The set of voxel data has a range of voxel values; furthermore, each voxel datum (i.e., each individual voxel) has at least a voxel value and an attribute value, such as a transparency value.

In one embodiment of the invention, a computerized system includes three components: a characteristic selector, a level point and window set, and a viewer. The characteristic selector permits a user to interactively select a characteristic from a plurality of characteristics. Each characteristic differently controls an attribute of the set of voxel data. The level point and window set permits the user to interactively set the level point and the window within the range of voxel values, where the window is centered at the level point and the characteristic selected is at least applicable within the window of such voxel values. Finally, the viewer responsively displays the set of voxels on a display device, such that the attribute values of voxel data having voxel values within the window are changed, as governed by the characteristic selected.

The characteristics are desirably preset to specific types of voxel data for clinical reasons to promote optimal viewing of the set of voxel data. Thus, a user will initially have selected for him or her a characteristic that corresponds to a given type of voxel data (i.e., MR, CT, etc.), along with the window and the location thereof. The user is also able, however, to select a different characteristic, and set the window and level point himself or herself. Setting the window means setting the window's width (i.e., a range of voxel values), while setting the level point sets the voxel value at which the window is centered. Voxels within the set of voxel data having voxel values within the window have their corresponding attribute values (e.g., transparency values, etc.) changed as governed by the characteristic. For example, a characteristic that is a "ramp," ramping from maximum transparency at one side of the window to minimum transparency at the other side of the window, causes the transparency of voxels having voxel values within the window to be changed accordingly.

In varying embodiments of the invention, computerized system, computerized methods, computers and data structures are disclosed. Still other and further aspects, advantages and embodiments of the invention will become apparent by reading the following specification, and by reference to the drawings.

DETAILED DESCRIPTION OF THE INVENTION

In the following detailed description of the preferred embodiments, reference is made to the accompanying drawings which form a part hereof, and in which is shown by way of illustration specific preferred embodiments in which the inventions may be practiced. These embodiments are described in sufficient detail to enable those skilled in the art to practice the invention, and it is to be understood that other embodiments may be utilized and that logical, mechanical and electrical changes may be made without departing from the spirit and scope of the present invention. The following detailed description is, therefore, not to be taken in a limiting sense, and the scope of the present invention is defined only by the appended claims.

The detailed description is divided into four sections. In the first section, a description of a typical computer in conjunction with which embodiments of the invention may be implemented is provided. In the second section, an exemplary characteristic, as applied to windows centered around level points, are presented. In the third section, a description of data structures, computerized systems, and computerized methods in accordance with one embodiment of the invention is given. Finally, in the fourth section, a conclusion is presented.

Computer

Figure 1:
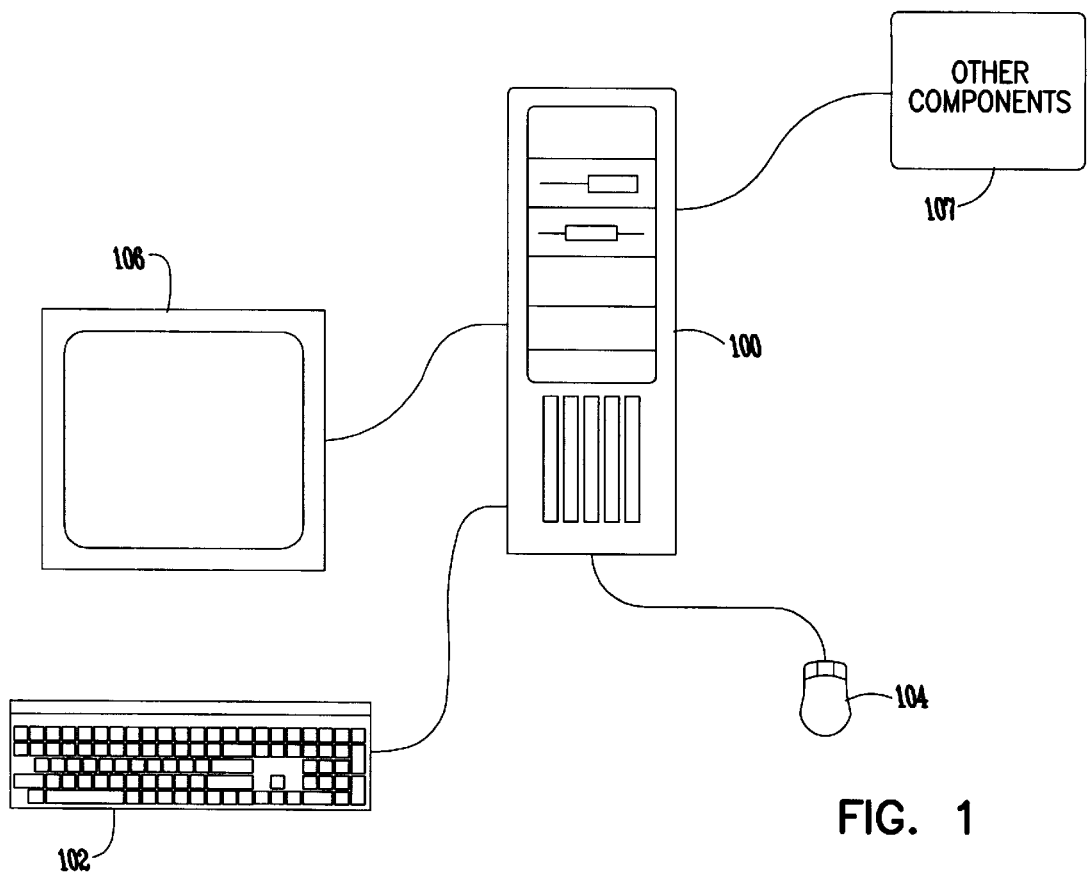
FIG. 1 is a diagram of a typical computer in conjunction with which embodiments of the invention may be implemented.

In this section of the detailed description, a description of a typical computer in conjunction with which embodiments of the invention may be implemented is provided. Referring to FIG. 1, the hardware shown includes computer 100, keyboard 102, pointing device 104, display device 106, and other components 107 (represented by a block diagram). Computer 100 is in one embodiment UNIX compatible. More particularly, computer 100 in one embodiment is a Silicon Graphics, Inc. (SGI) workstation running in an OSF/Motif window environment, with a graphical user interface. Such SGI workstations include the SGI O2, which in one embodiment runs the SGI Irix 6.3 operating system, in which case the embodiment is based on the OpenGL graphics library, and uses the Viewkit class library. The invention is not limited, however, to any particular computer 100.

As shown in FIG. 1, pointing device 104 is a mouse, although the invention is not limited to any particular pointing device. For example, pointing device 104 may also be a point stick, trackball, or a touch pad. The pointing device typically has three buttons, although no embodiment of the invention is so particularly limited. As described herein, clicking, selecting, pressing, or holding, etc., of a pointing device button (such as a mouse button) refers to the clicking, selecting, pressing, or holding, etc., of the left button if there is more than one button on the pointing device.

In one embodiment of the invention, an additional pointing device (viz., part of other components 107 as shown in FIG. 1) is also coupled to computer 100. This additional pointing device is a three-dimensional controller, which allows a user of the invention easy control of the fly through feature of embodiments of the invention. One such pointing device is the Spacetec IMC SpaceBall 3003. Display device 106 can be any of a number of different devices, but in one embodiment of the invention is a computer monitor having a cathode ray tube (CRT). In the embodiment of the invention where computer 100 is an SGI workstation, display device 106 is a twenty-one inch monitor capable of displaying twenty-four-bit color graphics, and having a resolution of 1280×1024 pixels. Furthermore, other components 107 may in varying embodiments of the invention include a video cassette recorder, or a printer. Computer 100 may also have the capability of hooking up to a network (such as a DICOM network), may having Internet or intranet capability, or have access to a DICOM server. Each of these is well known to those skilled in the art.

Not shown in FIG. 1 is that computer 100 typically includes a central-processing unit (CPU), a random-access memory (RAM), and a read-only memory (ROM). The CPU, RAM, and ROM may be of any type; no embodiment of the invention is particularly limited. In the embodiment of the invention where computer 100 is an SGI workstation, the CPU is a MIPS R10000 or an R5000, and there are typically one-hundred-twenty-eight megabytes of RAM. Also not shown in FIG. 1 is that computer 100 also usually comprises a fixed storage device such as a hard disk drive, and a removable storage device such as a tape cartridge drive or floppy disk drive. Conversely, such components may be external components to computer 100, in which case they are a part of other components 107. The tape cartridge drive in one embodiment is compatible with a General Electric Genesis tape archive format. The memory (e.g., RAM and ROM) and the storage devices (e.g., hard drives, floppy disks, tapes, etc.), are types of computer-readable media.

The invention provides an environment in which volume data comprised of voxels is displayed. No embodiment of the invention is limited as to the programming language by which the software aspect providing this environment is implemented. However, in one embodiment, the language is the object-oriented programming language C++. Furthermore, no embodiment of the invention is limited as to what the volume data comprised of voxels represents. In one embodiment of the invention, the volume data (voxel data) represents medical images of various parts of the human body, as scanned in from a medical imaging device. One embodiment of the invention specifically relates to the viewing of volume-related medical images; however, it should be understood to and appreciated by those of ordinary skill within the art that no embodiment of the invention is so limited.

An Exemplary Characteristic, as Applied to Windows Centered Around Level Points

In this section of the detailed description, an exemplary characteristic, as applied to windows centered around level points, in accordance with one embodiment of the invention, are described. As has been stated, a volume-rendered image includes a set of voxel data—that is, a set of individual voxel datums or "voxels." Each voxel has a voxel value, such that the set of voxel data has a range of voxel values, spanning from the lowest voxel value for any voxel within the set, to the highest voxel value for any voxel within the set. Furthermore, each voxel has at least one attribute value. An attribute value is a value corresponding to an attribute for a particular voxel. For example, a transparency value is an attribute value known in the art. The invention is not particularly limited to any given type of attribute values.

Figure 2A:
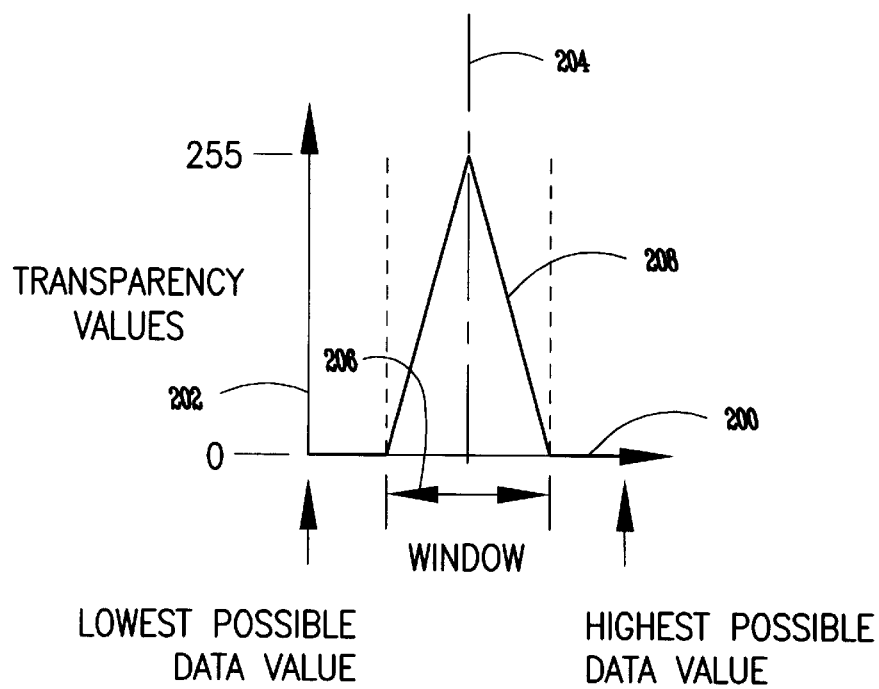
FIGS. 2(a) and 2(b) are diagrams of an exemplary spike characteristic, as applied to windows centered around level points.

Each of FIGS. 2($a$) and 2($b$) is a diagram of a characteristic, as applied to a window centered around a level point. Specifically, FIG. 2($a$) and FIG. 2($b$) are diagrams of a spike characteristic. Those of ordinary skill within the art can appreciate that the invention is not specifically limited to any given type of characteristic, such as the spike characteristic. Other characteristics include the ramp characteristic and the inverted spike characteristic. The spike characteristic described herein is used for exemplary and descriptive purposes only.

Referring first to FIG. 2($a$), the x-axis 200 maps voxel values, from the lowest possible voxel value for a given set of voxel data, to the highest possible voxel value for a given set of voxel data. Against this x-axis is defined level point 204, which is the center point for window 206. Window 206 is measured as a particular width of voxel values. It is moved along x-axis 200 by increasing or decreasing level point 204. Assuming that window 206 has a width W voxel values, and level point 204 is at L voxel values on x-axis 200, then window 206 has a lower limit defined as L−(W/2), and an upper limit defined as L+(W/2). That is, in absolute terms, window W extends from L−(W/2) to L+(W/2) on x-axis 200. Note that the width W and the level point L are integers, such that the expressions L−(W/2) and L+(W/2) are also integers (either truncated or rounded if the expressions does not by itself yield an integer). In one embodiment of the invention, voxel values are twelve bits in length.

Still referring to FIG. 2($a$), the y-axis 202 maps attribute values, such as transparency values, from their minimum to their maximum. Thus, setting a transparency value of zero for a given voxel value means that all voxels having this given voxel value have their transparency values set to zero—in other words, they are completely transparent, and cannot be seen. Conversely, setting a transparency value of maximum (in the case of eight-bit transparency values, 255), means that all voxels having this given voxel value have their transparency values set to maximum —in other words, they are completely opaque, and can be seen.

Characteristic 208 as shown in FIG. 2($a$) is a spike. A spike is defined as having an attribute value of zero at the upper and lower limits of window 206, an attribute value of maximum at level point 204, increasing linearly from zero at the lower limit of window 206 to maximum at level point 204, and decreasingly linearly from maximum at level point 204 to the upper limit of window 206. Desirably, for voxel values less than the lower limit of window 206, the attribute value is set to the attribute value at the lower limit of window 206 (that is, zero), and for voxel values greater than the upper limit of window 206, the attribute value is set to the attribute value at the upper limit of window 206 (that is, zero).

Therefore, characteristic 208 promotes the following optimal viewing of the set of voxel data against which characteristic 208 is applied. Characteristic 208 is applicable at least within window 206 to control an attribute of the set of voxel data, such that the attribute values of voxel data having voxel values within the window are governed by the characteristic. Thus, assuming the attribute controlled by characteristic 208 is transparency, voxels having voxel values equal to L—corresponding to level point 206—are seen the most, since they are the most opaque. Thus, the closer a voxel's voxel value is to L, the more it can be seen, since as governed by the characteristic, the closer the voxel's voxel value is to L, the higher the opacity. Once a voxel's voxel value is less than or greater than L by W/2 or more (corresponding to the lower and upper limits of window 206, respectively), the voxel no longer is seen, since it becomes completely transparent.

Figure 2B:
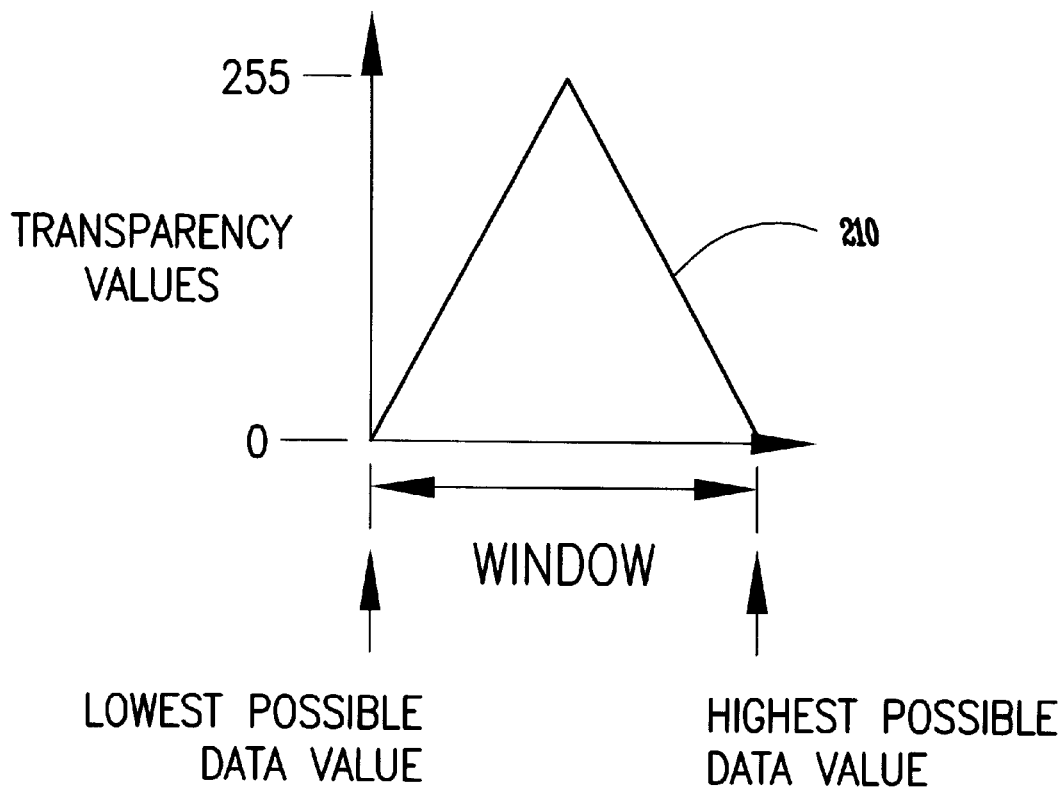

In this manner, a characteristic permits precise viewing of a given type of data. Characteristics are configurable. For example, the spike characteristic of FIG. 2(a) has a window of width W, where W is less than the highest possible voxel value minus the lowest possible voxel value. Referring next to FIG. 2(b), however, a diagram of another spike characteristic is shown. Spike characteristic 210 of FIG. 2(b), however, has a width equal to the highest possible voxel value minus the lowest possible voxel value, plus one. Thus, while spike characteristic 208 of FIG. 2(a) permits the opacity of voxels having only a small slice of voxel values, spike characteristic 210 of FIG. 2(b) permits the opacity of voxels having a slice of voxel values extending over the entire range of possible voxel values.

Furthermore, characteristics are desirably preset to specific types of voxel data for clinical reasons to promote optimal viewing of the set of voxel data. Thus, while the spike characteristics of FIG. 2(a) and FIG. 2(b) may be useful in a certain application, other characteristics may be useful in other application. Such other characteristics may include the ramp characteristic and the inverted spike characteristic, although as has been stated, the invention is not so limited.

Data Structures, Computerized Systems, and Computerized Methods

Figure 3A:
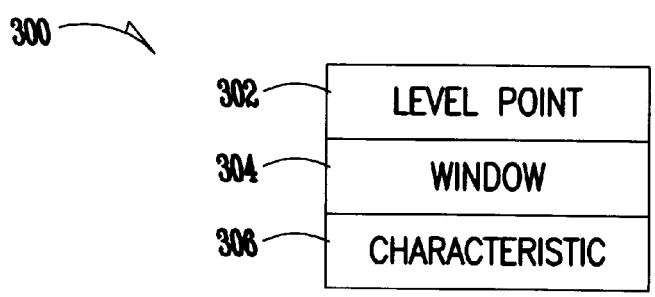
FIG. 3(a) is a diagram of a data structure in accordance with one embodiment of the invention.

In this section of the detailed description, data structures, computerized systems, and computerized methods according to one embodiment of the invention are shown. Referring first to FIG. 3(a), a diagram of a data structure according to one embodiment of the invention is shown. Data structure 300 has three data fields, data fields 302, 304 and 306. Data field 302 includes first data representing a level point within the range of voxel values for a given set of voxel data, as has been described in the previous section. Data field 304 includes second data representing a window within the range of voxel values and centered at the level point, as has also been described in the previous section. Finally, data field 306 includes third data representing a predetermined characteristic at least applicable within the window to control an attribute of the set of voxel data, such that the attribute values of voxel data having voxel values within the window are governed by the characteristic, as has also been described in the previous section.

Referring next to FIG. 3(b), a diagram of a representative screen shot of a computerized system in accordance with one embodiment of the invention is shown. Screen 310 of a display device of the computerized system includes screen shot 312. Within display area 314 is displayed a given set of voxel data representing an object. A characteristic is chosen via list 316, which may include characteristics such as spike, ramp, etc. Within window 318 the selected characteristic is displayed. The width of window 318 is controlled in one of two ways: by decreasing or increasing the lower limit of the window by dragging handle 320, or by decreasing or increasing the upper limit of the window by dragging handle 322. Conversely, handle 324 corresponds to the level point, such that dragging it causes translational movement of window 318, since window 318 by definition is centered at the level point.

Desirably, selecting a new characteristic from list 316, controlling the window via handles 320 and 322, or controlling the level point via handle 324, causes responsive change in the display of the set of voxel data as displayed in area 314. Specifically, the responsive change in the display of the set of voxel data is in accordance with the manner by which the characteristic selected in 316, as configured via handles 320, 322 and 324, governs the attribute displayed in attribute area 326. Thus, a user of the system is permitted interactive selection of the characteristic via list 316, which acts as a characteristic selector, as well as interactive setting of the level point and the window via handles 320, 322 and 324, which act as a level point and window set. This interactive selection and setting causes responsive display of the set of voxel data in accordance with the configured characteristic within area 314, which acts as a viewer.

Those of ordinary skill within the art will recognize that the exemplary screen shot shown in FIG. 3(b) may desirably be the result of the execution of a computer program by the processor of the computer from a computer-readable medium of the computer, such as memory or a storage device, as have been described. That is, such a computer program causes the computer to change the attribute values of voxel data having voxel values within the window as governed by the characteristic. The computer program also causes the computer to change the attribute values of other voxel data as has been described herein.

It is noted, however, that the computerized system, an exemplary screen shot of which is shown in FIG. 3(b), is representative of one embodiment of the invention. The invention itself, however, is not so limited. That is, a representative characteristic selector, level point and window set, and viewer have been shown in and described in conjunction with FIG. 3(b). The invention is not so limited to the representative characteristic selector, level point and window set, and viewer that have been shown in and described in conjunction with FIG. 3(b), however.

Figure 3C:
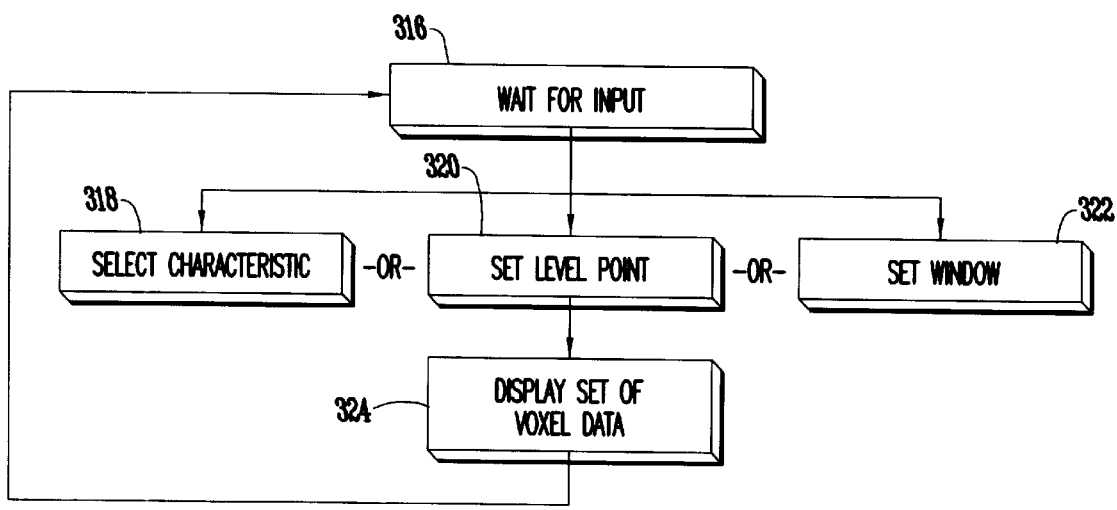
FIG. 3(b) is a diagram of a representative screen shot of a computerized system in accordance with one embodiment of the invention; and, FIG. 3(c) is a flowchart of a computerized method in accordance with one embodiment of the invention.

The desirable interactive and responsive nature of one embodiment of the invention is shown more clearly by reference to FIG. 3(c), which is a flowchart of a computerized method in accordance with one embodiment of the invention. Input is waited for in step 316. This input may either by the selection of a characteristic of a plurality of characteristics to control an attribute of the set of voxel data (step 318), the setting of the level point within the range of voxel values (step 320), or the setting of the window within the range of voxel values, such that the window is centered at the level point and the characteristic is at least applicable within the window (step 322). Depending on whether the user is selecting a characteristic, setting the level point, or setting the window, the appropriate of step 318, 320 or 322 is proceeded to.

However, regardless of which of steps 318, 320 and 322 is proceeded to, control next proceeds to step 324, in which the set of voxel data is redisplayed in accordance with the changes made in the previous step. That is, the set of voxel data is displayed on a display device, such that the attribute values of voxel data having voxel values within the window are changed as governed by the characteristic selected. After the set of voxel data is redisplayed, control proceeds back to step 316, and the method starts over again.

Thus, this embodiment of the invention is interactive and responsive in that a user is able to provide an input (step 318, 320 or 322), and immediately see the results of that input (step 324). The interactive nature of this embodiment of the invention comes about from the method waiting for an input (step 316) after every time a display of the set of voxel data is done (step 324). The responsive nature of this embodiment of the invention originates from the method displaying the set of voxel data (step 324), after each input is processed (step 318, 320 or 322). The interactive and responsive nature of this embodiment is an advantage of the invention.

Conclusion

Controlling the attributes of volume-rendered images via a window/level mechanism when the images are displayed has been described. Although specific embodiments have been illustrated and described herein, it will be appreciated by those of ordinary skill in the art that any arrangement which is calculated to achieve the same purpose may be substituted for the specific embodiments shown. This application is intended to cover any adaptations or variations of the present invention. Therefore, it is manifestly intended that this invention be limited only by the following claims and equivalents thereof.

I claim:

1. A data structure to assist in displaying a set of voxel data representing an object on a display device of a computer, the set of voxel data having a range of voxel values, each voxel datum of the set of voxel data having at least a voxel value and a transparency value, the structure comprising:

first data representing a level point within the range of voxel values;

second data representing a window within the range of voxel values and centered at the level point; and, third data representing a predetermined characteristic at least applicable within the window to control transparency of the set of voxel data, such that the transparency values of voxel data having voxel values within the window are governed by the characteristic.

2. The data structure of claim 1, wherein the window has a lower limit, and the transparency values of voxel data having voxel values less than the lower limit are governed by the characteristic at the lower limit.

3. The data structure of claim 1, wherein the window has an upper limit, and the transparency values of voxel data having voxel values greater than the upper limit are governed by the characteristic at the upper limit.

4. The data structure of claim 1, wherein the characteristic is preset for clinical reasons to promote optimal viewing of the set of voxel data.

5. The data structure of claim 1, wherein the characteristic is also configurable.

6. The data structure of claim 1, wherein the characteristic is selected from the group consisting of: a spike characteristic, a ramp characteristic, and an inverted spike characteristic.

7. A computer to assist in displaying a set of voxel data representing an object, the set of voxel data having a range of voxel values, each voxel datum of the set of voxel data having at least a voxel value and a transparency value, the computer comprising:

a processor;

a computer-readable medium storing first data representing a level point within the range of voxel values, second data representing a window within the range of voxel values and centered at the level point, and third data representing a predetermined characteristic at least applicable within the window to control transparency of the set of voxel data; and, a computer program executed by the processor from the medium to cause the computer to change the transparency values of voxel data having voxel values within the window as governed by the characteristic.

8. The computer of claim 7, wherein the window has a lower limit, and the computer program changes the transparency values of voxel data having voxel values less than the lower limit as governed by the characteristic at the lower limit.

9. The computer of claim 7, wherein the window has an upper limit, and the computer program changes the transparency values of voxel data having voxel values greater than the upper limit as governed by the characteristic at the upper limit.

10. The computer of claim 7, wherein the characteristic is selected from the group consisting of: a spike characteristic, a ramp characteristic, a double-hump characteristic, an inverted spike characteristic, and a double spike characteristic.

11. A computerized system to assist in displaying a set of voxel data representing an object on a display device, the set of voxel data having a range of voxel values, each voxel datum of the set of voxel data having at least a voxel value and a transparency value, the system comprising:

a characteristic selector to permit a user to interactively select a characteristic of a plurality of characteristics to control transparency of the set of voxel data;

a level point and window set to permit a user to interactively set the level point within the range of voxel values, and interactively set the window within the range of voxel values, the window centered at the level point and the characteristic at least applicable within the window; and, a viewer to responsively display the set of voxel data on the display device, such that the transparency values of voxel data having voxel values within the window are changed as governed by the characteristic selected.

12. The computerized system of claim 11, wherein the window has a lower limit, and the viewer also displays the set of voxel data such that the transparency values of voxel data having voxel values less than the lower limit are changed as governed by the characteristic at the lower limit.

13. The computerized system of claim 11, wherein the window has an upper limit, and the viewer also displays the set of voxel data such that the transparency values of voxel data having voxel values greater than the upper limit are changed as governed by the characteristic at the upper limit.

14. A computerized method to assist in displaying a set of voxel data representing an object on a display device of a computer, the set of voxel data having a range of voxel values, each voxel datum of the set of voxel data having at least a voxel value and a transparency value, the method comprising:

interactively selecting a characteristic of a plurality of characteristics to control transparency of the set of voxel data;

interactively setting a level point within the range of voxel values;

interactively setting a window within the range of voxel values, the window centered at the level point and the characteristic at least applicable within the window; and, displaying the set of voxel data on the display device, such that the transparency values of voxel data having voxel values within the window are changed as governed by the characteristic selected.

15. The computerized method of claim 14, wherein the window has a lower limit, and the set of voxel data is also displayed such that the transparency values of voxel data having voxel values less than the lower limit are changed as governed by the characteristic at the lower limit.

16. The computerized method of claim 14, wherein the window has an upper limit, and the set of voxel data is also displayed such that the transparency values of voxel data having voxel values greater than the upper limit are changed as governed by the characteristic at the upper limit.

17. The computerized method of claim 14, wherein interactively selecting a characteristic selects a spike characteristic.

18. The computerized method of claim 14, wherein interactively selecting a characteristic selects a ramp characteristic.

19. The computerized method of claim 14, wherein interactively selecting a characteristic selects an inverted spike characteristic.

20. The computerized method of claim 14, wherein interactively selecting a characteristic selects a double-hump characteristic.

* * * * *